US012622794B2

(12) United States Patent
Büchert et al.

(10) Patent No.: US 12,622,794 B2
(45) Date of Patent: May 12, 2026

(54) MEDICAL DEVICE FOR TREATING ANEURYSMS

(71) Applicant: Acandis GmbH, Pforzheim (DE)

(72) Inventors: Michael Büchert, Pforzheim (DE); Giorgio Cattaneo, Karlsruhe (DE)

(73) Assignee: Acandis GmbH, Pforzheim (DE)

( * ) Notice: Subject to any disclaimer, the term of this patent is extended or adjusted under 35 U.S.C. 154(b) by 889 days.

(21) Appl. No.: 17/632,774

(22) PCT Filed: Jul. 21, 2020

(86) PCT No.: PCT/EP2020/070501
§ 371 (c)(1),
(2) Date: Feb. 4, 2022

(87) PCT Pub. No.: WO2021/028162
PCT Pub. Date: Feb. 18, 2021

(65) Prior Publication Data
US 2022/0273472 A1 Sep. 1, 2022

(30) Foreign Application Priority Data
Aug. 9, 2019 (DE) .......................... 102019121562.5

(51) Int. Cl.
*A61F 2/90* (2013.01)
*A61F 2/82* (2013.01)

(52) U.S. Cl.
CPC .......... *A61F 2/90* (2013.01); *A61F 2002/823* (2013.01); *A61F 2250/0067* (2013.01)

(58) Field of Classification Search
CPC ........ A61F 2002/823; A61F 2/07; A61F 2/90; A61B 17/12113
See application file for complete search history.

(56) References Cited

U.S. PATENT DOCUMENTS 5,554,182 A 9/1996 Dinh et al.
5,571,166 A * 11/1996 Dinh ....................... A61L 31/16
600/36

(Continued)

FOREIGN PATENT DOCUMENTS

DE 69623855 T2 5/2003
EP 0578998 A1 * 1/1994 ............... A61F 2/90

(Continued)

OTHER PUBLICATIONS

German Examination Report, German Application No. 10 2019 121 562.5, dated May 28, 2020, 8 pages.

(Continued)

*Primary Examiner* — Seema Mathew
(74) *Attorney, Agent, or Firm* — Cesari and McKenna, LLP

(57) ABSTRACT

The invention relates to a medical device for treating aneurysms, in particular a stent, including a compressible and expandable grid structure made up of grid elements. The grid structure has at least one closed cell ring which includes at most 12, in particular at most 10, in particular at most 8, in particular at most 6 cells directly adjacent to one another in a circumferential direction of the grid structure. The grid structure is provided at least in certain portions with a covering made of an electrospun fabric which has pores of irregular sizes. The covering includes over a surface area of 100 000 μm2 at least 10 pores which have a size of at least 15 μm2. The covering has a biocompatible, in particular antithrombogenic and/or endothelialization-promoting coating.

18 Claims, 4 Drawing Sheets

(56) References Cited

U.S. PATENT DOCUMENTS

| | | | |
|---|---|---|---|
| 9,005,695 B2 | 4/2015 | Shank et al. | |
| 9,320,592 B2 * | 4/2016 | Wainwright | A61P 9/00 |
| 2001/0020086 A1 * | 9/2001 | Hubbell | C07K 14/475 |
| | | | 530/322 |
| 2008/0036113 A1 | 2/2008 | Chun et al. | |
| 2008/0109055 A1 * | 5/2008 | Hlavka | A61F 2/95 |
| | | | 623/1.1 |
| 2009/0053281 A1 * | 2/2009 | Richard | A61B 17/12022 |
| | | | 606/200 |
| 2009/0054966 A1 | 2/2009 | Rudakov et al. | |
| 2009/0275974 A1 * | 11/2009 | Marchand | A61B 17/12118 |
| | | | 87/8 |
| 2011/0301696 A1 | 12/2011 | Mangiardi | |
| 2014/0058498 A1 | 2/2014 | Hannes et al. | |
| 2014/0081414 A1 * | 3/2014 | Hall | A61L 31/10 |
| | | | 264/413 |
| 2015/0112419 A1 * | 4/2015 | Ahn | A61L 27/507 |
| | | | 623/1.13 |
| 2017/0079661 A1 * | 3/2017 | Bardsley | A61F 2/90 |
| 2018/0104044 A1 | 4/2018 | Zhao et al. | |
| 2018/0110637 A1 | 4/2018 | Kealey et al. | |
| 2022/0273472 A1 * | 9/2022 | Büchert | A61F 2/90 |

FOREIGN PATENT DOCUMENTS

| | | | | |
|---|---|---|---|---|
| EP | 2796112 A1 | 10/2014 | | |
| EP | 2678466 B1 | 2/2016 | | |
| EP | 2982392 A1 | 2/2016 | | |
| EP | 2946750 B1 | 7/2017 | | |
| EP | 2546394 B1 | 4/2018 | | |
| WO | WO-2002049536 A2 | 6/2002 | | |
| WO | WO-2008024669 A2 * | 2/2008 | | A61P 39/00 |
| WO | WO-2012113581 A1 * | 8/2012 | | A61L 31/146 |
| WO | WO-2014177634 A1 | 11/2014 | | |
| WO | WO-2022126021 A1 * | 6/2022 | | A61L 27/20 |

OTHER PUBLICATIONS

PCT Notification of Transmittal of the International Search Report and the Written Opinion of the International Searching Authority, or the Declaration, International Searching Authority, International Application No. PCT/US2020/070501, mailed Oct. 21, 2020, 14 pages.

* cited by examiner

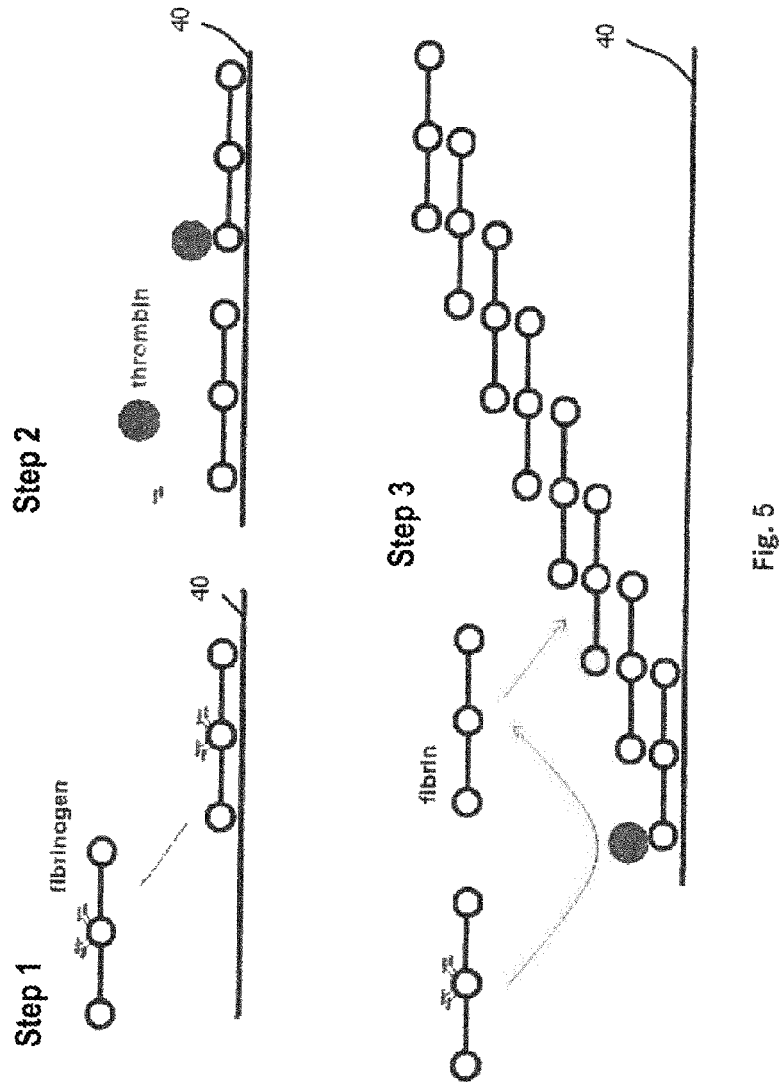

MEDICAL DEVICE FOR TREATING ANEURYSMS

CROSS REFERENCE TO RELATED APPLICATIONS

The present application is a National Stage of International Application No PCT/EP2020/070501, fled Jul. 21, 2020, which application claims priority to commonly owned German Patent Application No. 102019121562.5, filed on Aug. 9, 2019, which applications are incorporated herein by reference in their entirety.

TECHNICAL FIELD

The invention relates to a medical device for the treatment of aneurysms, in particular a stent, in accordance with the preamble of patent claim 1. An example of a medical device of the aforementioned type is known from the Applicant's document WO 2014/177634 A1.

BACKGROUND

WO 2014/177634 A1 describes a highly flexible stent which has a compressible and expandable mesh structure, wherein the mesh structure is formed in one piece. The mesh structure comprises closed cells which are each delimited by four mesh elements. The mesh structure has at least one cell ring which comprises between three and six cells.

Furthermore, to the Applicant's knowledge, stents with mesh structures are known which are produced from a single wire. The wire is braided with itself in order to form a tubular network. At the axial ends of the tubular network, the wire is curved round so that loops which act atraumatically are formed. The axial ends may flare outwards in a funnel shape. The mesh elements of such mesh structures are therefore formed by at least one wire, wherein the respective wire sections which extend between two points of intersection in an expanded state of the mesh structure are defined as mesh elements.

The known medical device is particularly suitable for the treatment of aneurysms in small cerebral blood vessels. Blood vessels of this type have a very small cross sectional diameter and are often highly tortuous. For this reason, the known stent is highly flexible in configuration, so that on the one hand it can be compressed to a very small cross sectional diameter, and on the other hand it has a high bending flexibility, which enables it to be delivered to small cerebral blood vessels.

For the treatment of aneurysms in cerebral blood vessels, it is advantageous to use stents which bridge an aneurysm and screen it from the flow of blood inside the blood vessel. To enable this, providing stents with a covering is known; it occludes the cells of the stent and thus prevents a flow of blood into an aneurysm. Coverings of this type are often produced from textile materials. In combination with the stent structure, however, this results in a relatively thick-walled stent, whereupon again, the compressibility of the stent is compromised. Thus, the covering limits compression to a small cross sectional diameter, which in turn hinders delivery of the stent to small cerebral blood vessels. The Applicant's document EP 2 946 750 B1 tackles the problem of the compressibility of a stent with a textile covering by producing fibrous strands of the textile material from loosely ordered individual filaments.

The prior art discloses textile-like structures which are suitable for covering aneurysms. In particular, EP 2 546 394

A1 discloses a covering of this type, what is known as a graft, which has an electrospun structure. In order to obtain a particularly low porosity, a plurality of layers of this electrospun structure are overlaid. However, this results in thick walls which are a problem when delivering to small, highly tortuous blood vessels.

From WO 02/49536 A2, an electrospun structure is also known which has two layers of electrospun fabric, wherein the two layers have different porosities. Here again, the walls are relatively thick and hence the compressibility of the electrospun structure is limited.

EP 2 678 466 B1 concerns a stent for neurovascular applications which is covered with a nonwoven fabric. The nonwoven fabric is produced by electrospinning and comprises a plurality of layers, wherein an inner layer is impermeable to liquid and an outer layer is sponge-like in configuration. Thus, the nonwoven fabric forms a membrane with very low permeability to liquid and because of the sponge-like layer, the walls are thick, which compromises the compressibility of the stent.

When treating aneurysms using a medical device with a mesh structure in a main blood vessel, so that the mesh structure lies over the neck of the aneurysm, it has proved to be advantageous for endothelial colonization to occur. In this way, the medical device becomes integrated into the blood vessel and in the end, the tissue formed by the endothelial cells can seal off the aneurysm from the main blood vessel. The disadvantage with prior art medical devices, however, is that it is difficult for the endothelial cells to form on the mesh structure, and in particular because of the size of the cells of the mesh structure, the entire mesh structure is not evenly covered or complete coverage occurs only slowly, because the tissue has to bridge a relatively large gap between two webs or wires or wire sections of a mesh structure.

SUMMARY

In the light of this prior art, the objective of the invention is to provide a medical device for the treatment of aneurysms, in particular a stent, which can be compressed down to be very small and at the same time produces good, long-lasting endogenous coverage of an aneurysm.

In accordance with the invention, this objective is achieved by the subject matter of patent claims 1 and 3.

The inventive concept therefore pertains to a medical device for introduction into a hollow body organ, in particular a stent, with a compressible and expandable mesh structure produced from mesh elements. The mesh structure has at least one closed cell ring which comprises at most 12, in particular at most 10, in particular at most 8, in particular at most 6, immediately adjacent cells in a circumferential direction of the mesh structure. The cell ring may in particular comprise at least 3 cells which are immediately adjacent in a circumferential direction of the mesh structure. At least a section of the mesh structure is provided with a covering produced from electrospun fabric which has irregular pores. In a preferred variation, the covering comprises at least 10 pores with a size of at least 15 $\mu m^2$ over an area of 100000 $\mu m^2$. The invention also provides that the covering has a biocompatible, in particular antithrombogenic and/or endothelialization-promoting coating.

In a preferred configuration, the medical device, in particular the stent, preferably its mesh structure, is self-expandable. This has the advantage that the medical device can be fed via very small catheters and upon expansion of the mesh structure, on the one hand does not radially load a vessel wall unduly, but on the other hand permanently and correctly holds it well.

Particularly preferably, the covering has at least 10 pores with a size of at least 30 $\mu m^2$ over an area of 100000 $\mu m^2$.

In particular, the at least 10 pores may have an inscribed circle diameter of at least 4 $\mu m$, in particular at least 5 $\mu m$, in particular at least 6 $\mu m$, in particular at least 7 $\mu m$, in particular at least 8 $\mu m$, in particular at least 9 $\mu m$, in particular at least 10 $\mu m$, in particular at least 12 $\mu m$, in particular at least 15 $\mu m$, in particular at least 20 $\mu m$. The inscribed circle diameter is the diameter of the largest possible circle which can be inscribed in the pore. In other words, the inscribed circle diameter corresponds to the external diameter of a cylinder which can just be pushed through the pore.

The invention combines a highly flexible mesh structure as a support structure with a covering which has a high permeability or porosity and is particularly thin and flexible because of its production method. In this respect, the medical device is on the whole extremely compressible and can readily be introduced into very small blood vessels.

Good stability of the support structure or the mesh structure is achieved by the fact that the mesh structure has a closed cell ring which has at most 12 immediately adjacent cells in the circumferential direction of the mesh structure. The closed cell ring also means that after partial release, the mesh structure can be pulled back into a catheter since no mesh elements which could become stuck on the tip of the catheter protrude out because of the closed structure. In particular, all of the cell rings of the mesh structure have at most 12, in particular at most 10, in particular at most 8, in particular at most 6 immediately adjacent cells in the circumferential direction of the mesh structure. It is possible for all of the cell rings to comprise at least 3 cells which are immediately adjacent in a circumferential direction of the mesh structure.

By limiting the cells in the circumferential direction to a cell ring, the mesh elements as well as their connectors or points of intersection are also limited. Because of the limited number of mesh elements in the circumferential direction, the mesh structure can be compressed to a small cross sectional diameter in which the mesh elements preferably lie immediately adjacent to each other. Moreover, by limiting the cells in the circumferential direction, a higher bending flexibility can also be obtained, so that the mesh structure, in particular even in the compressed state, can be fed by means of a catheter through narrow, highly tortuous vessels.

A high flexibility, in particular bending flexibility, of the mesh structure can be obtained by making the webs of a cell in the case of mesh structures which are formed in one piece (i.e. not braided from wires) have different flexibilities. Thus, advantageously, a cell may be produced from two web pairs which respectively have two webs running parallel to each other. Thus, overall, the cell has a total of four webs which are disposed in a manner such that the cells substantially form a diamond shape. In each case, two opposing webs form one web pair. The webs of a first web pair may be more flexible than the webs of a second web pair. The higher flexibility may be obtained by the shape of the webs, their materials and/or their web width, web thickness and/or web length. Preferably, the webs of a cell have a web width of between 25 $\mu m$ and 50 $\mu m$, in particular between 30 $\mu m$ and 40 $\mu m$. The web thickness is advantageously between 40 $\mu m$ and 70 $\mu m$, in particular between 50 $\mu m$ and 60 $\mu m$.

In the case of mesh structures which are braided from a single wire or a plurality of wires, advantageous flexibility is obtained when the braided mesh structure has a braiding angle between 60° and 70°, preferably 65°. The wire thickness of a braided mesh structure of this type is preferably between 40 $\mu m$ and 60 $\mu m$, in particular 50 $\mu m$. In the circumferential direction, the mesh structure preferably comprises between 6 and 10, in particular between 6 and 8 cells or meshes.

Furthermore, the coating of the electrospun covering promotes the formation of an endothelial cell tissue which results in long-lasting endogenous covering of an aneurysm. The endothelial cell tissue is particularly stable and/or fluid-tight, but at the same time has a similar flexibility to the surrounding vessel walls. The endothelial cell tissue can therefore successfully follow a pulse wave in a blood vessel and therefore reduces the risk of vessel stenosis.

In particular, the combination of the antithrombogenic and/or endothelialization-promoting coating with the electrospun covering is particularly effective. The small pore size of the covering in itself promotes the colonization of endothelial cells, which is further improved by the coating. In this way, the endothelial cell tissue is built up particularly rapidly, so that the overall healing process following installation of the medical device can be accelerated by means of a minimally-invasive surgical intervention. This in turn reduces the length of a hospital stay for a patient.

Antithrombogenic properties prevent the formation of thrombi in the main lumen, but at the same time allow perfusion in side branches. Thus, the combination of the electrospun covering, which has a small average pore size, with a biocompatible, in particular antithrombogenic or endothelialization-promoting coating is advantageous. In the small pores, the endothelium grows where small pressure gradients prevail, especially at the vessel wall and at the neck of the aneurysm. This is further promoted by the endothelialization-promoting properties of the coating. At the same time, perfusion with blood is ensured through the pores with the preferred minimum side, where strong pressure gradients arise, i.e. in particular in the region of branching vessels. In addition to the lower limit for the pore size, in this case coating with an antithrombogenic substance is advantageous.

Furthermore, it is possible to embed antithrombogenic and/or endothelialization-promoting substances into the material of the electrospun covering before the covering is formed with this material by means of the electrospinning process.

Preferably, the mesh elements delimit closed cells of the mesh structure, wherein each closed cell is delimited by four respective mesh elements. The mesh elements run between points of intersection or connection points of the mesh elements, preferably in substantially straight lines. The mesh elements could also in fact have a curved form, in particular an S-shaped form. The curvature between two points of intersection or connection points, however, will be at most 90°.

High stability of the mesh structure is obtained by means of the closed cells; this is advantageous to the function of the mesh structure as a support for the covering. In particular, a high stability in the axial direction, i.e. in the direction of a longitudinal axis of the mesh structure, is obtained, which improves delivery of the medical device through a catheter. In the radial direction, because of the closed cells, the flexibility of the mesh structure may be increased, which results in an improved radial force.

The covering, which is formed by an electrospun fabric, enables an aneurysm to be covered, but at the same time allows for a certain permeability for blood until formation of the endothelial cell tissue is complete. This permeability is advantageous, so that the cells of the aneurysm wall can be supplied with nutrients. In this manner, degeneration of the cells and the risk of a possible rupture of the aneurysm is avoided until the endothelial cell tissue has been formed and so long-lasting endogenous covering of the aneurysm is obtained.

Particularly advantageously, the porous electrospun covering is generally perfusible. When the medical device covers not only an aneurysm but also a blood vessel which branches off close to the aneurysm, then the pressure gradient which is set up at the branching blood vessel between the inside and the outside of the covering allows perfusion of the covering. It has been shown to be advantageous that in this region, as a rule, no endothelial cell tissue is formed because of the pressure gradient, so that the branching blood vessel is permanently supplied with blood. It is only in the region of the aneurysm at which the covering results in a reduction in the flow in the aneurysm and therefore the pressure gradient is reduced to practically zero, that endothelial cell tissue is rapidly formed which occludes the aneurysm. The rapid formation of the endothelial cell tissue is in particular obtained by the combination of the preferred pore size for the covering as defined herein with the coating.

In an electrospun fabric, pores are usually irregularly shaped. However, the production method does not permit the pores to be formed in a particular pattern or shape. Furthermore, the pore sizes can only be adjusted by means of the process parameters in order to ensure that at least a portion of the pores have a certain minimum size. In accordance with the invention, over an area of 100000 $\mu m^2$, a minimum number of pores is present which in turn have a minimum size. Specifically, over an area of 100000 $\mu m^2$, at least 10 pores are present with a size of at least 15 $\mu m^2$, in particular at least 30 $\mu m^2$. In practice, this combination of a specific minimum number of pores and a minimum size for these pores has proved to be particularly necessary for sufficient blood permeability for the covering with good coverage at the same time.

During production of the covering, the minimum size of the pores can be adjusted, in particular via the duration of the electrospinning process. In addition, the covering produced from an electrospun fabric is extremely thin and flexible, which adds to the flexibility of the mesh structure. In particular, the covering barely inhibits the mesh structure from compression, which is in contrast to prior art coverings which are produced from other textile materials. Overall, then, the entire medical device in accordance with the invention can be compressed to a much smaller cross sectional diameter, and thus can be fed by means of small catheters through particularly small blood vessels.

By means of the medical device in accordance with the invention, therefore, treatments are also possible in blood vessels which could not be accessed with medical devices of the prior art which have a mesh structure and a covering. Because of the high compressibility of the device in accordance with the invention, very low delivery forces arise when delivering via a catheter. In addition, the material of the covering can contribute to reducing the delivery forces. In particular, the delivery forces for the device with a covering may be only slightly higher, the same or lower, compared with delivering the mesh structure alone. In any event, the delivery forces in the device with a covering compared to delivering the mesh structure alone are at most 50%, in particular at most 25%, in particular at most 10% higher.

The advantages of the present invention are even further improved when the covering, as is preferred, comprises at least 15 pores with a size of at least 30 $\mu m^2$, in particular at least 50 $\mu m^2$, in particular at least 70 $\mu m^2$, in particular at least 90 $\mu m^2$ over an area of 100000 $\mu m^2$. It is also advantageous for the covering to have at least 15, in particular at least 20, in particular at least 25, pores with a size of at least 30 $\mu m^2$ over an area of 100000 $\mu m^2$.

In order to ensure that the permeability of the covering is not too high, i.e. medically acceptable coverage of the aneurysm from the blood flow in the vessel is obtained, in a preferred variation of the invention, the pore size is at most 750 $\mu m^2$, in particular at most 500 $\mu m^2$, in particular at most 300 $\mu m^2$. The upper limit for the pore size defined here prevents the network from becoming too unstable.

In a variation of the invention, the medical device has a coating at least part of which comprises fibrin. Fibrin has a very stable network structure on a molecular level. As a result, the coating comprising fibrin is very long-lasting and robust, so that the medical device can be fed through smaller catheters, for example catheters below 3 Fr, than with prior art coatings.

Preferably, the coating is stable or long-lasting insofar as the mass of the coating is reduced by a maximum of 5%, in particular by a maximum of 3%, in particular by a maximum of 1% over a time period of at least four hours, in particular at least 30 days when it comes into contact with blood or a physiological replacement fluid, in particular with a sodium chloride solution or Ringer's lactate solution. This ensures that the coating is effective over a sufficiently long period of time.

The coating may be long-lasting insofar as the mass of the covering remains entirely constant upon contact with blood or a physiological replacement fluid, for example a sodium chloride solution or Ringer's lactate solution, over a time period of at least four hours, in particular at least 30 days. A period of time such as this, for example, enables blood components, especially proteins, to be deposited on the mesh structure or the covering, which then ensure cell proliferation in the context of endothelialization. The anti-thrombogenic coating therefore bridges the time period from introduction to natural covering or encapsulation of the medical device with a neointimal layer, in particular produced from endothelial cells which are formed around the networked structural elements.

The use of a physiological replacement fluid to test the long-term stability/durability of the coating enables an objective comparison to be made. Furthermore, by using the replacement fluid, which advantageously resembles human blood, this means that objective empirical data can be determined therefrom, allowing conclusions to be drawn regarding the behaviour of the covering when in the implanted state when the covering is exposed to a flow of human blood. Thus, the replacement fluids used are preferably a 0.9 percent sodium chloride solution or Ringer's lactate solution. Replacement fluids of this type are isotonic and are suitable for use as indicators for the behaviour of the covering in the implanted state.

In order to prevent detachment of the coating when guiding the medical device through a catheter, the coating is preferably abrasion-resistant. In particular, the coating can be abrasion-resistant insofar as the mass of the coating is reduced by a maximum of 30%, in particular by a maximum of 20%, in particular by a maximum of 10%, in particular by a maximum of 5%, when the covering on which the coating is formed is pushed once through a catheter with a length of 155 cm to 165 cm. The coating may furthermore be abrasion-resistant insofar as the mass of the coating is completely stable when the medical device is passed once through a catheter with a length of 155 cm to 165 cm. The abrasion-resistance is preferably such that at least 80%, in particular at least 90%, in particular at least 95%, in particular 100% of the covering remains intact.

A coating with a layer thickness of at least 10 nm is advantageous. This ensures that the abrasion-resistance will be sufficient.

Preferably, at least part of the coating comprises heparin. The heparin may be covalently bonded to the fibrin and/or embedded in the fibrin. The term "embedded" as used here should be understood to mean that the heparin which is covalently bonded to the fibrin coating forms an integral component of the coating and is incorporated into the coating. The heparin which is covalently bonded to the fibrin coating can therefore be present both at the surface as well as in the interior of the coating. In each of these scenarios, the heparin is covalently bonded to the fibrin coating, preferably to the filaments of fibrin.

The coating may be produced such that a layer of fibrin is applied to a mesh structure or to the covering and then heparin is covalently bonded to this layer of fibrin. Covalent binding of the heparin to the layer of fibrin continues until the heparin is embedded in the fibrin layer. The term "embedded" should be understood to mean that the heparin which is covalently bonded to the fibrin coating forms an integral component of the coating and is incorporated into the coating. In this manner, heparin is not only on the surface, but is also present in the interior of the coating.

The coating comprising fibrin may be produced from a fibrinogen solution with antithrombin III and heparin and functionalized by covalent bonding of chemically activated heparin. The functionalized coating of fibrin may contain between 0.5 $\mu g/cm^2$ and 3 $\mu g/cm^2$, in particular between 1.0 $\mu g/cm^2$ and 2.0 $\mu g/cm^2$, in particular between 1.2 $\mu g/cm^2$ and 1.6 $\mu g/cm^2$, in particular between 1.3 $\mu g/cm^2$ and 15 $\mu g/cm^2$ of fibrin, and between 5 $mU/cm^2$ and 50 $mU/cm^2$, in particular between 7 $mU/cm^2$ and 30 $mU/cm^2$, in particular between 10 $mU/cm^2$ and 20 $mU/cm^2$, in particular 12 $mU/cm^2$ to 18 $mU/cm^2$, particularly preferably 15 $mU/cm^2$ of heparin, wherein 180 U of heparin corresponds to 1 mg of heparin; these values may vary by ±20%. The functionalized coating considerably improves the haemocompatibility of the covering.

The quantity of fibrin may be measured with the aid of a bicinchoninic acid (BCA) assay kit. The BCA method allows the concentration of a protein such as fibrin to be measured in a solution. The quantity of heparin may be measured with the aid of a colorimetric assay.

The covering may be securely connected to the mesh structure, in particular cohesively connected. In particular, the covering may be applied directly to the mesh structure. As an example, the electrospinning process may be carried out directly on the mesh structure, so that when the covering is being formed, a connection with the mesh structure is produced at the same time. The covering may be cohesively connected to the mesh structure. Alternatively or in addition, the coating may be cohesively connected to the covering. In particular, the coating may be adhered to a surface of the covering. Preferably, the coating is attached to the covering by means of physical adsorption. The coating may be bonded to the covering over the entire surface.

The covering may be cohesively connected to the mesh structure by means of an adhesive bond. The adhesive bond may comprise or consist of a bonding agent produced from polyurethane.

The secure connection between the covering and the mesh structure prevents detachment of the covering from the mesh structure when feeding the medical device through a catheter. At the same time, positioning of the medical device under X-ray monitoring is facilitated, because either the mesh structure or the covering may be provided with appropriate radiographic markers. Because the relative position between the covering and the mesh structure remains constant, additional radiographic markers which could identify any relative displacement between the covering and the mesh structure are not necessary. Overall, then, the number of radiographic markers, for example radiographic marker sleeves, can be reduced, which in turn has a positive effect on the compressibility of the medical device.

It is also possible for at least a portion of the coating to be embedded in the covering or be admixed with the material of the covering. In particular, the fibrin and the heparin (preferably covalently bonded to the fibrin) may also be integrated into the material of the covering. Specifically, fibrin and heparin may be homogeneously embedded in the synthetic material which forms the covering. The fibrin and the heparin in this case are not (only) on the surface, but also within the volume of the covering.

The mesh elements of the mesh structure may be sheathed with a bonding agent, in particular polyurethane. In particular, the bonding agent may form the cohesive connection between the covering and the mesh structure. Preferably, the bonding agent surrounds the entire mesh element and in this manner forms a sheath for the mesh element.

In a preferred further embodiment of the mesh structure configured as a hollow body, the hollow body is entirely perfusible along the longitudinal axis. A configuration of the mesh structure of this type enables the medical device to be used as a stent or flow diverter which barely inhibits a blood flow through the blood vessel in the longitudinal direction, but prohibits the inflow of blood into a branched aneurysm because of the covering, or at least reduces the inflow.

In a preferred configuration of the invention, the covering is disposed on an outside of the mesh structure. In this situation, the mesh structure forms a support structure which applies a sufficient radial force to fix the covering against a vessel wall. In this regard, the support structure supports the externally disposed covering. As an alternative, the covering may also be disposed on an inside of the mesh structure.

As an alternative or in addition, the covering may be disposed on an inside of the mesh structure. In particular, the mesh structure may be embedded between two coverings which are each formed by an electrospun fabric. The mesh elements of the mesh structure can therefore be completely sheathed by the electrospun fabric. Specifically, the electrospun fabric of a covering on the inside of the mesh structure extends through the cells of the mesh structure and is connected to the electrospun fabric of a covering on the outside of the mesh structure. The mesh elements which delimit the cells are therefore sheathed on all sides by electrospun fabric.

The coating preferably completely surrounds the covering. In particular, the coating may completely sheath all of the filaments of the electrospun covering.

Preferably, the covering is produced from a synthetic material, in particular a polyurethane. Materials of this type are particularly light and can readily be produced in fine filaments by an electrospinning process. The synthetic material therefore means that on the one hand, a particularly thin and fine-pored covering can be produced. On the other hand, the synthetic material already has a high intrinsic flexibility, so that a high compressibility of the medical device is obtained.

A contribution to the flexibility of the covering is also made when, as is preferable, the covering is produced from filaments disposed in an irregular network and which have a filament thickness of between 0.1 μm and 3 μm, in particular between 0.2 μm and 2 μm, in particular between 0.5 μm and 1.5 μm, in particular between 0.8 μm and 1.2 μm.

Particularly preferably, the medical device is a stent for the treatment of aneurysms in arterial, in particular neuro-vascular, blood vessels. Preferably, the blood vessels may have a cross sectional diameter of between 1.5 mm and 5 mm, in particular between 2 mm and 3 mm. It is also possible to treat blood vessels with a cross sectional diameter of 4 mm to 8 mm. Carotid arteries, for example, have cross sectional diameters of this size.

In general, the medical device may be a stent for the treatment of saccular or fusiform aneurysms. Particularly in the case of fusiform aneurysms, i.e. aneurysms which extend over the entire circumference of a blood vessel, advantageously, a deliberately fine-pored structure is used for the colonization of endothelial cells; this is promoted by the coating. In this manner, the defective vessel wall can be reconstructed. Specifically, the structure provided with a specific pore size which is formed by the electrospun fabric forms a scaffold for colonization by endothelial cells which can then form a new, closed vessel wall. A treatment of fistulae, dissections and other malformations is also possible with the embodiments of the invention. In addition, stenoses and arteriosclerosis can be treated with the medical device in accordance with the invention. For applications of this type and also for other applications, it may be advantageous for the coating to additionally have anti-inflammatory properties.

The electrospun structure has openings. These openings change their shape and size as a function of the vessel diameter and the manipulation of the implant and therefore provide unique and changing conditions for cellular proliferation.

With regard to the permeability and regularity of the covering, advantageously, at least 60%, in particular at least 70%, in particular at least 80% of the area of the covering is formed by pores with a size of at least 5 μm², in particular at least 10 μm². In particular, at least 30% of the area of the covering may be formed by pores with a size of at least 30 μm². It is also possible for at least 40%, in particular at least 50%, in particular at least 60%, in particular at least 70%, in particular at least 80%, of the area of the covering to be formed by pores with a size of at least 30 μm². The aforementioned values have been shown to be advantageous to the production of a covering which has a specific minimum permeability, in order to obtain a sufficient supply of nutrients to the cells in an aneurysm.

In order to ensure that the covering is sufficiently dense to shield the aneurysm from the flow of blood in the blood vessel in order to prevent a further extension of the aneurysm, it has been shown to be advantageous for at most 20% of the area of the covering to be formed by pores with a size of at least 500 μm². Alternatively or in addition, at most 50% of the area of the covering may be formed by pores with a size of at least 300 μm².

In general, the mesh structure may be configured as a single-pieced mesh structure. It is also possible for the mesh structure to be produced from a wire which is braided with itself or from a plurality of wires which are braided together. In this regard, in preferred embodiments, the mesh elements form webs which are coupled together by means of web connectors (one-piece mesh structure). As an alternative, the mesh elements may form wire sections of wires which are braided with each other (braided mesh structure). The mesh elements may also form wire sections of a single wire which is braided with itself in order to form the braided mesh structure. While a braided mesh structure is characterized by a particularly high flexibility, in particular bending flexibility, a one-piece mesh structure has comparatively thin walls, so that the mesh structure influences the blood flow inside a blood vessel to a lesser extent.

Particularly preferably, the braided mesh structure is produced from a single wire which is curved round at the axial ends of the tubular mesh structure and forms atraumatic end loops. The wire may have a radiopaque core material and a sheath material produced from a shape memory alloy. In particular, the volume ratio between the core material, preferably platinum, and the volume of the whole of the composite wire is between 20% and 40%, in particular between 25% and 35%.

At the axial ends, the mesh structure may flare radially, in particular in the manner of a funnel. The flaring angle is preferably between 50° and 70°, in particular between 55° and 65°. The cells may be disposed in cell rings which extend in the circumferential direction of the braided mesh structure, wherein the rings have 6 to 12 cells, in particular 6 to 10 cells.

In general, the mesh structure (one-piece or braided) is preferably self-expandable.

BRIEF DESCRIPTION OF THE DRAWINGS

The invention will now be explained in more detail with the aid of exemplary embodiments and with reference to the accompanying drawings, in which:

FIG. 5 shows a diagrammatic representation of the formation of the fibrin nanostructure on a covering.

DESCRIPTION

Figure 1:
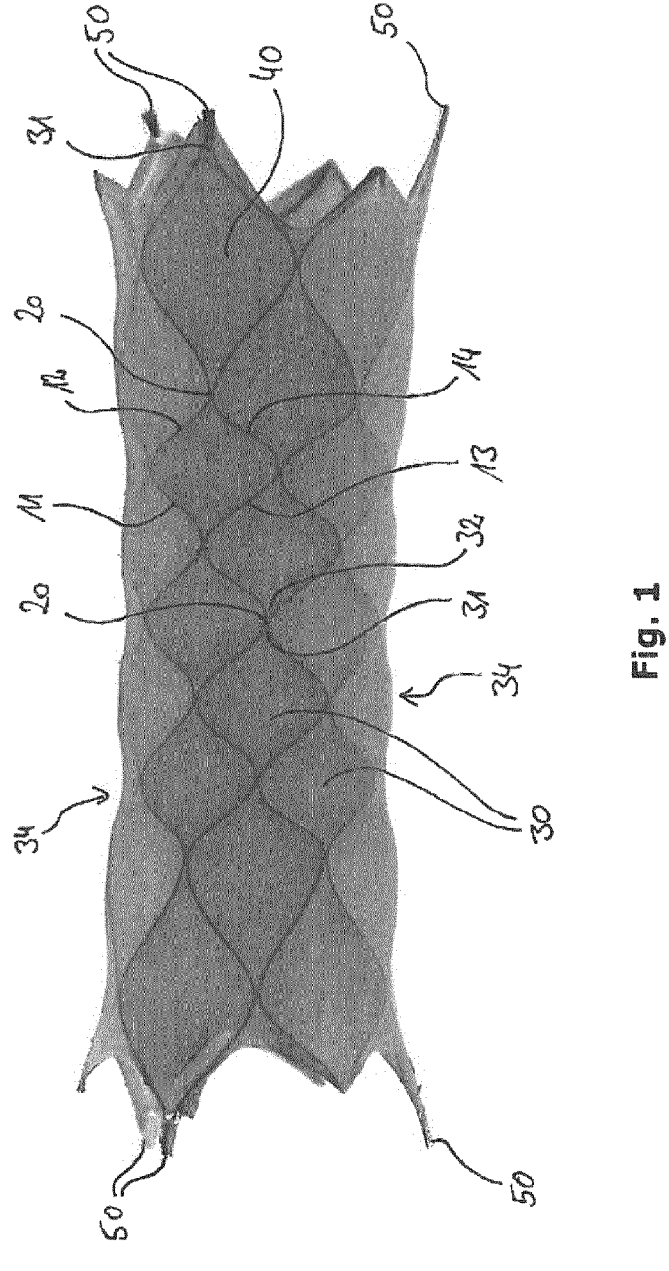
FIG. 1 shows a side view of a medical device in accordance with the invention according to a preferred exemplary embodiment.

The accompanying figures show a medical device which is suitable for introduction into a hollow body organ. In particular, the medical device enables aneurysms, preferably in cerebral blood vessels, to be treated.

In this regard, the medical device in particular has a mesh structure 10 which is compressible and expandable. In other words, the mesh structure 10 may take up a delivery state, in which the mesh structure 10 has a relatively small cross sectional diameter. The mesh structure 10 is preferably self-expandable, so that the mesh structure 10 can expand by itself to a maximum cross sectional diameter without the influence of external forces. The state in which the mesh structure 10 has the maximum cross sectional diameter corresponds to the expanded state. In this state, the mesh structure does not exert any radial forces.

It should be noted that in the context of the present application, all of the dimensional information and/or geometric shapes for the medical device are given in respect of the expanded state of the mesh structure, unless indicated otherwise.

Preferably, the mesh structure 10 is one-piece in configuration. In particular, at least portions of the mesh structure 10 may be cylindrical. Preferably, the mesh structure 10 is produced from a tubular blank by laser cutting. In this regard, individual mesh elements or webs 11, 12, 13, 14 of the mesh structure 10 are exposed by the laser cutting process. The regions removed from the blank form cells 30 of the mesh structure 10.

The cells 30 have a substantially diamond-shaped basic shape. In particular, the cells 30 are delimited by four respective webs 11, 12, 13, 14. The webs 11, 12, 13, 14 in the exemplary embodiment which is depicted here have an at least partially curved profile, in particular S-shaped. Other shapes for the webs are possible.

The cells 30 each have cell tips 31, 32 which form the corner points of the diamond-shaped basic shape. The cell tips 31, 32 are respectively disposed at web connectors 20 which each connect four webs 11, 12, 13, 14 together into one piece. Four respective webs 11, 12, 13, 14 extend from each web connector 20, whereupon two cells 30 are associated with each web 11, 12, 13, 14. The webs 11, 12, 13, 14 respectively delimit the cell 30.

FIG. 1 shows the mesh structure 10 in the expanded state. It can readily be seen that the web connectors 20 are substantially respectively disposed on a common circumferential line. Overall, then, a plurality of cells 30 form a cell ring 34 in the circumferential direction of the mesh structure 10. A plurality of cell rings 34 connected together in the longitudinal direction form the entire mesh structure 10. In the exemplary embodiment shown, the cell rings 34 each comprise six cells 30.

In this regard, it should be noted here that the mesh structure 10 may be formed by interconnected cell rings which have the same cross sectional diameter only in sections. In fact, it is also possible for sections of the mesh structure 10 to have a geometry which differs from that of a cylinder. As an example, the mesh structure may be funnel-shaped at least at a proximal end. A configuration of this type is advantageous in medical devices which are employed to capture thrombi or, more generally as thrombectomy devices. In these cases, the mesh structure 10 may essentially form a basket-like structure.

Mesh structures 10 which are completely cylindrical in configuration are in particular used in medical devices which form a stent. Stents can be used to support blood vessels or, more generally, hollow body organs and/or to cover aneurysms.

When the mesh structure 10 is deployed from a catheter, or generally a feeding system, the mesh structure 10 automatically expands radially outwardly. In this regard, the mesh structure 10 passes through a plurality of levels of expansion until the mesh structure 10 reaches the implanted state. In the implanted state, the mesh structure 10 preferably exerts a radial force on the surrounding vessel walls. In the implanted state, the mesh structure 10 preferably has a cross sectional diameter which is approximately 10%-30%, in particular approximately 20% smaller than the cross sectional diameter of the mesh structure 10 in the expanded state. The implanted state is also described as the "intended use configuration".

As can readily be seen in FIG. 1, radiographic markers 50 are provided in the medical device. The radiographic markers 50 are disposed at cell tips 31, 32 on the edge cells 30 of the mesh structure 10. Specifically, the radiographic markers 50 may be formed as radiopaque sleeves, for example produced from platinum or gold, which are crimped onto the cell tips 31, 32 of the edge cells 30. In FIG. 1, it can be seen that each longitudinal end of the mesh structure 10 has three respective radiographic markers 50.

The mesh structure 10 of FIG. 1 can be divided into three sections. Two edge sections, which are each formed by two cell rings 34, are connected via a central section which comprises five cell rings 34. The cells 30 of the central section essentially have a diamond-shaped geometry, wherein all of the webs 11, 12, 13, 14 of the cells 30 of the central section have substantially the same length. The edge cell rings 34 each comprise cells in which two of the immediately adjacent webs 11, 12, 13, 14 in the circumferential direction are each longer in configuration than the two webs 11, 12, 13, 14 of the same cell 30 which are adjacent in the axial direction. In this manner, the edge cells 30 essentially form a kite-like basic shape.

The medical device of FIG. 1 furthermore comprises a covering 40 which is disposed on an outside of the mesh structure 10. The covering 40 bridges the entire mesh structure 10 and in particular covers the cells 30. The covering 40 is produced from an electrospun fabric and is therefore characterized by a particularly thin wall. At the same time, the covering 40 is sufficiently stable to follow an expansion of the mesh structure 10. Preferably, the covering 40 is completely and securely connected to the mesh structure 10. Specifically, the covering 40 is preferably bonded to the webs 11, 12, 13, 14, for example by means of a bonding agent which is applied to the mesh structure 10 by means of a dip coating process.

The covering 40 may extend over the entire mesh structure 10, as can be seen in FIG. 1. Alternatively, it is possible for the covering 40 to extend over only a portion of the mesh structure 10. As an example, edge cells at one axial end or at both axial ends of the mesh structure 10 may be without a covering. In this regard, the covering 40 may stop before the last or penultimate cell ring 34 of the mesh structure 10. The cell rings 34 which are without a covering allow for good coupling to a transport wire. In addition, the edge cells, which in any case barely participate in covering an aneurysm but are meant to serve as anchors in a blood vessel, provide a high permeability in this manner, so that the internal walls of the vessel can be properly supplied with nutrients in this region. The region of the medical device which has the covering 40 can be highlighted by radiographic markers.

Figure 2:
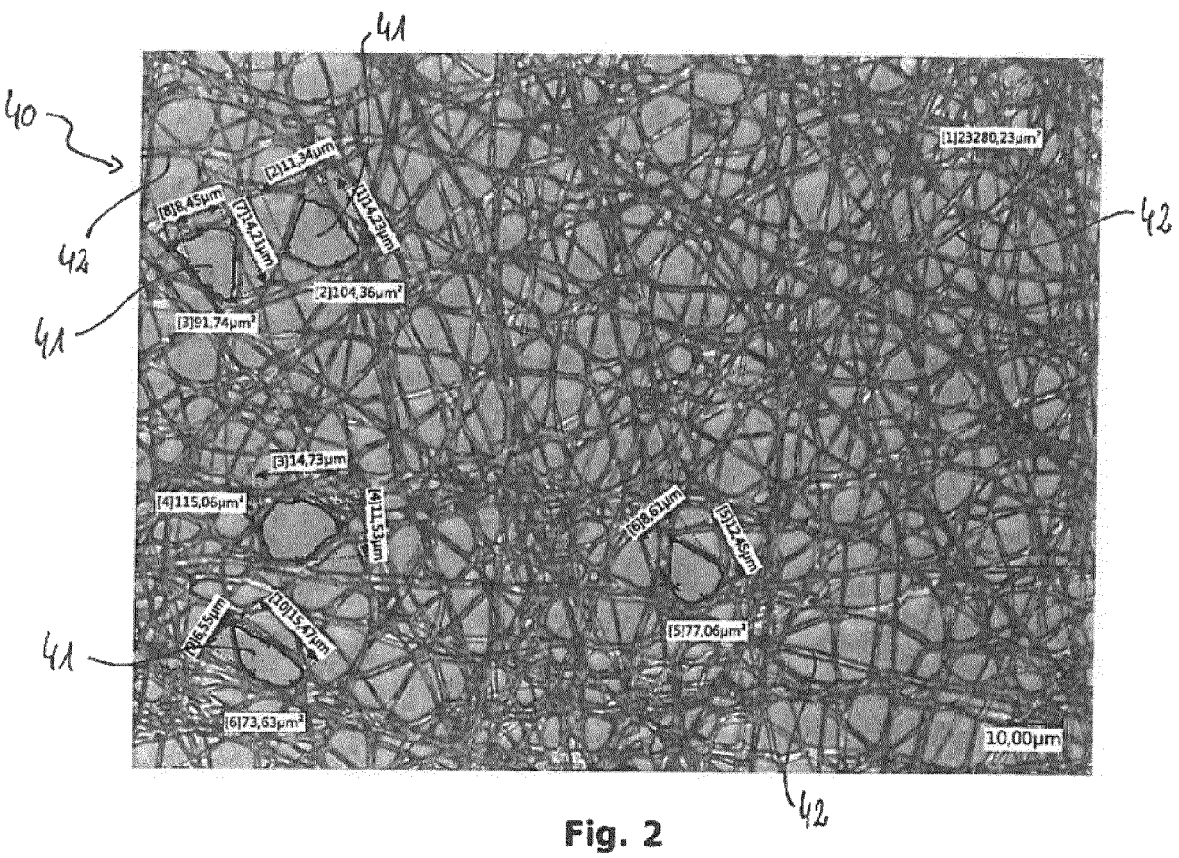
FIG. 2 shows a scanning electron microscope image of a covering of a medical device in accordance with the invention according to a preferred exemplary embodiment.
Figure 3:
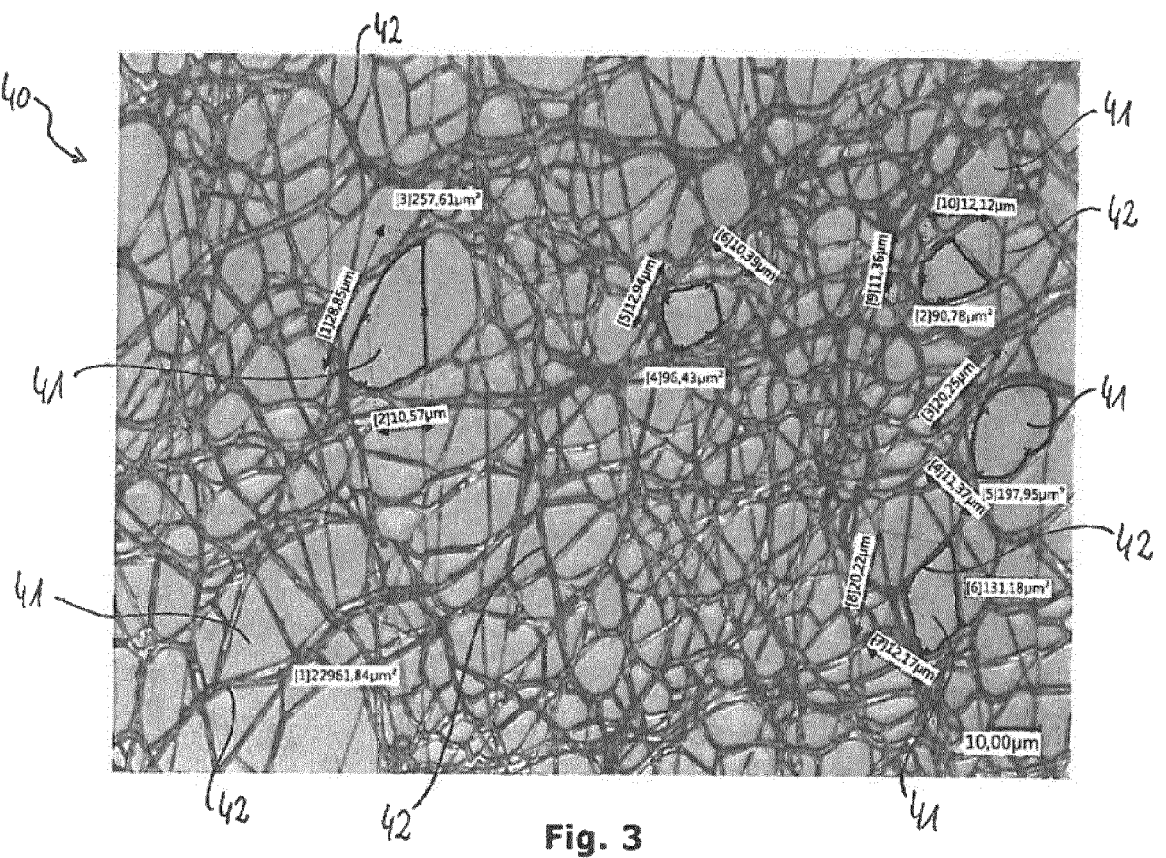
FIG. 3 shows a scanning electron microscope image of a covering of a medical device in accordance with the invention according to a further exemplary embodiment.

The construction of the covering 40 can readily be discerned from the scanning electron microscope images of FIGS. 2 and 3. These show that the covering 40 has a plurality of irregularly sized pores 41 which are each delimited by filaments 42. By means of the electrospinning process, a plurality of filaments 42 are formed which are orientated in an irregular manner with respect to each other. The pores 41 are formed in this manner. FIG. 2 also shows that the pores 41 have comparatively small pore sizes, wherein some pores 41 are sufficiently large, however, to ensure blood permeability. Specifically, in FIG. 2, four pores 41 with a size of more than 30 $\mu m^2$ have been graphically highlighted. The density of the pores 41 with a size of more than 30 $\mu m^2$ indicates that the covering has at least 10 pores 41 of this type over an area of 100000 $\mu m^2$.

In all of the exemplary embodiments, the covering 40 has a biocompatible, in particular antithrombogenic and/or endothelialization-promoting coating 45. The coating 45 covers the entire covering 40. Specifically, the filaments 42 of the covering 40 are each completely sheathed by the coating 45. This may be obtained, for example, by means of a dip coating process. The coating 45 is preferably produced from fibrin which contains covalently bonded heparin. The fibrin preferably binds to the metal surface of the mesh structure by physical adsorption.

The mesh structure is preferably produced from a metal. The coating 45 is preferably bonded to the mesh structure or the covering in a stable manner. In contact with tissue and/or blood or bodily fluids in general, the coating is gradually degraded. Until it has been completely degraded, the coating inhibits thrombus formation and promotes the formation of endothelial cell tissue which then, for example, completely shields an aneurysm from a main blood vessel. Thus, during the biological process, endothelial cells can be deposited on the coating and grow into tissue on the covering.

FIG. 3 shows a further exemplary embodiment of a covering 40, in which a generally larger pore size has been set. It can be seen that some pores 41 have a size of more than 30 $\mu m^2$ wherein, however, a pore size of 300 $\mu m^2$ is not exceeded.

FIGS. 2 and 3 respectively show that the filaments 42 of the covering 40 intersect multiple times. A particular feature of the electrospinning process is, however, that in the covering 40, sites are present at which exclusively two filaments intersect, i.e. no more than two filaments 42 intersect. It is clear from this that the overall covering 40 has very thin walls and is therefore highly flexible.

The high flexibility of the covering 40 in combination with the high flexibility of the mesh structure 10 means that a medical device, in particular a stent, can be provided which can be introduced into a blood vessel through very small delivery catheters. In particular, delivery catheters can be used with a size of 6 French, in particular at most 5 French, in particular at most 4 French, in particular at most 3 French, in particular at most 2 French. Specifically, in the exemplary embodiments described herein, the medical devices can be used in catheters which have an internal diameter of at most 1.6 mm, in particular at most 1.0 mm, in particular at most 0.7 mm, in particular at most 0.4 mm.

The layer thickness of the covering 40 in particularly preferred variations is at most 10 $\mu m$, in particular at most 8 $\mu m$, in particular at most 6 $\mu m$, in particular at most 4 $\mu m$. In this, at most 4, in particular at most 3, in particular at most 2 filaments 42 intersect. In general, within the electrospun structure of the covering 40, intersecting points are present in which only 2 filaments 42 intersect. Preferably, the mesh structure 10 has a cross sectional diameter of between 2.5 mm and 8 mm, in particular between 4.5 mm and 6 mm.

Figure 4:
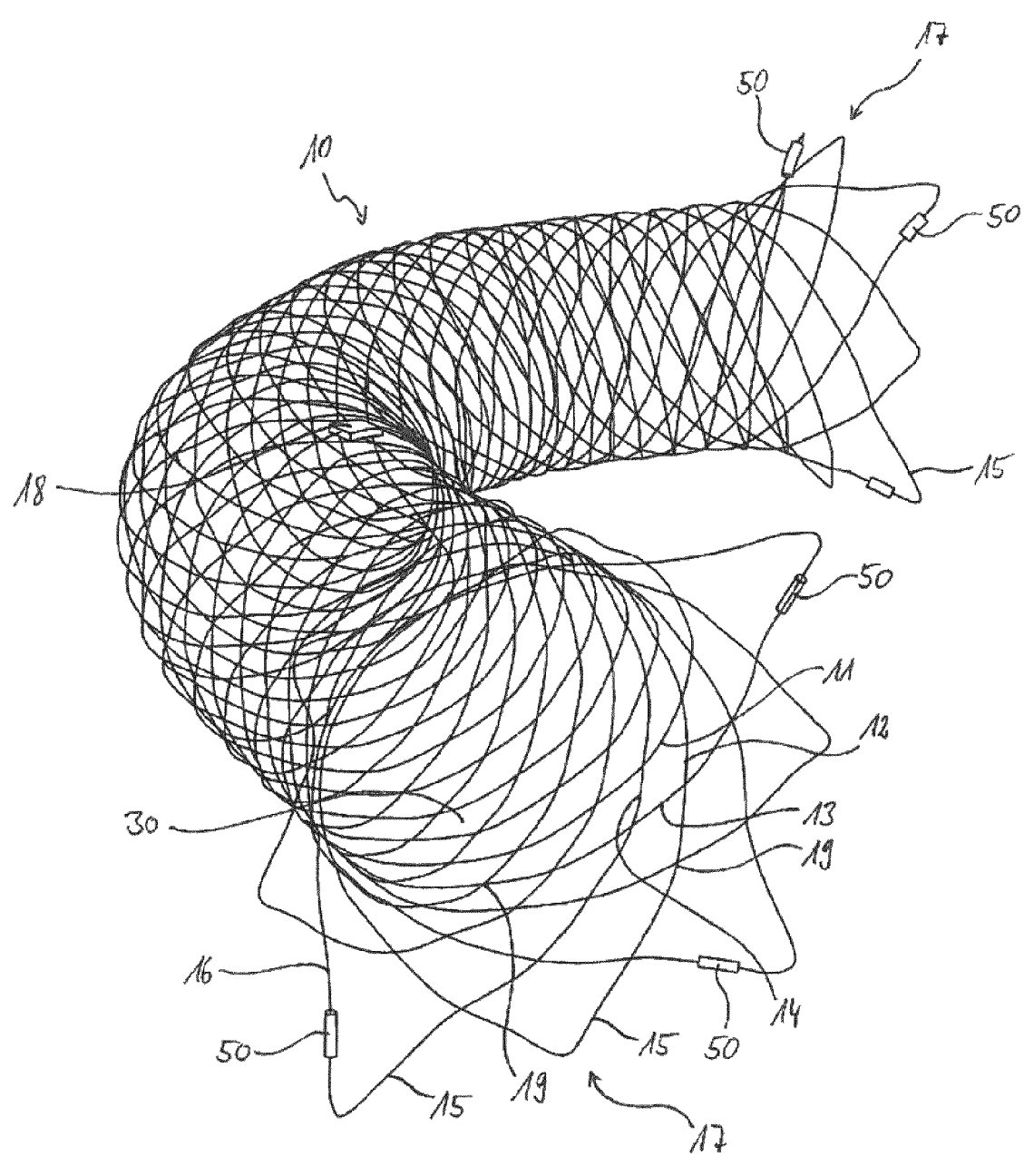
FIG. 4 shows a perspective view of a mesh structure of a medical device in accordance with the invention according to a further preferred exemplary embodiment.

FIG. 4 shows a braided mesh structure 10 which, in a preferred exemplary embodiment, can form a support for a covering 40. The braided mesh structure 10 is formed by a single wire 16 which is braided into a tube. The wire ends are connected within the mesh structure 10 with a connecting element 18.

The wire 16 has a plurality of sections which are described as the mesh elements 11, 12, 13, 14. Each section of the wire 16 which runs between two intersecting points 19 is described as an autonomous mesh element 11, 12, 13, 14. Clearly, four respective mesh elements 11, 12, 13, 14 delimit a mesh or cell 30.

The braided mesh structure 10 has flaring axial ends which are described as flares 17. The wire 16 is turned around in each flare 17 and forms end loops 15. Overall, in the exemplary embodiment shown, six end loops 15 are provided at each flare 17. Alternate end loops 15 carry a radiographic marker 50 in the form of a crimp sleeve. Thus, three respective radiographic markers 50 are present on each axial end of the mesh structure 10.

FIG. 5 shows the formation of the coating 45 produced from fibrinogen on a substrate surface, wherein the covering 40 in the exemplary embodiments described here provides the substrate surface. As can be seen in FIG. 5, fibrinogen can be applied to the surface of the covering 40 by absorption (step 1). Thus, when the surface is exposed to a thrombin solution, thrombin can be bound to the absorbed fibrinogen by means of a bio-specific, non-covalent bond (step 2). When the surface is then exposed to a solution of fibrinogen, the immobilized thrombin-fibrinogen which is generated on the surface from the solution is converted into fibrin monomers which then spontaneously form a network of fibrin filaments at the substrate surface (step 3).

The growth of the fibrin network can be stopped by replacing the fibrinogen solution by a buffer. The coating thickness may in particular be reduced when the anticoagulant antithrombin III is added to the fibrinogen solution. A very thin network of fibrin can be obtained by adding a mixture of antithrombin III and heparin. Antithrombin III and heparin are then removed from the final coating by washing with a buffer.

In this manner, the thickness of the coating 45 can be regulated by the user in any way, preferably to between 5 nm and 100 nm. The fibrin coating described above may be formed on almost any substrate, including the electrospun covering which preferably consists of polyurethane. The coating is biodegradable and biocompatible.

Furthermore, the heparin may be covalently bound to the fibrin of the coating 45, so that the heparin is embedded in the fibrin. The heparin which is covalently bound to the fibrin coating 45 can therefore be present both at the surface as well as in the interior of the coating 45.

The covalent bonding of one of the heparins to the coating 45, which consists of fibrin nanostructures, improves the haemocompatibility and promotes binding and proliferation of vascular endothelial cells.

The antithrombogenic coating with heparin bridges the time interval to natural healing or encapsulation of the medical device with a neointimal layer, in particular produced from endothelial cells, which form on the mesh elements 11, 12, 13, 14.

LIST OF REFERENCE NUMERALS

10 mesh structure

11, 12, 13, 14 web or mesh element

15 end loop

16 wire

17 flare

18 connecting element

19 intersecting point

20 web connector

30 cell

31, 32 cell tip

34 cell ring

45 coating

40 covering

41 pore

42 filament

50 radiographic marker

The invention claimed is:

1. A medical device for treatment of an aneurysm comprising:

a compressible and expandable mesh structure having at least one closed cell ring which includes at most 12 immediately adjacent cells in a circumferential direction of the mesh structure, wherein the mesh structure is provided, at least in sections, with a covering produced from an electrospun fabric having irregularly sized pores, which are each delimited by filaments, wherein the covering includes at least 10 pores with a size of at least 15 $\mu m^2$ over an area of 100000 $\mu m^2$, wherein the covering has a biocompatible coating, which completely sheaths all of the filaments of the covering, wherein at least part of the coating includes fibrin, and wherein at least part of the coating includes heparin.

2. The medical device according to claim 1, wherein the coating has a layer thickness of at least 10 nm.

3. The medical device according to claim 1, wherein one of the covering is cohesively connected to the mesh structure or the coating is cohesively connected to the covering.

4. The medical device according to claim 1, wherein the coating is bonded to a surface of the covering.

5. The medical device according to claim 4, wherein the coating has a thickness between 5 nm and 100 nm.

6. The medical device according to claim 1, wherein the mesh structure includes mesh elements sheathed by a bonding agent which securely connects the covering to the mesh structure.

7. The medical device according to claim 1, wherein the heparin is embedded in the fibrin.

8. The medical device according to claim 1, wherein at least part of the coating is one of admixed with a material of the covering or embedded in the covering.

9. The medical device according to claim 1, wherein the coating has between 0.5 $\mu g/cm^2$ and 3 $\mu g/cm^2$ of fibrin.

10. The medical device according to claim 1, wherein the coating has between 5 $mU/cm^2$ and 50 $mU/cm^2$ of heparin.

11. The medical device according to claim 1, wherein the mesh structure includes mesh elements that form webs coupled together into one piece by web connectors.

12. The medical device according to claim 1, wherein the mesh structure includes mesh elements formed by at least one wire.

13. The medical device according to claim 1, wherein the mesh structure has a closed cell design.

14. A medical device for treatment of an aneurysm comprising:

a compressible and expandable mesh structure having at least one closed cell ring which includes at most 12 immediately adjacent cells in a circumferential direction of the mesh structure, wherein the mesh structure is provided, at least in sections, with a covering produced from an electrospun fabric having irregularly sized pores which are each delimited by filaments, wherein the covering includes at least 10 pores with a size of at least 15 $\mu m^2$ over an area of 100000 $\mu m^2$, wherein the covering has one of an antithrombogenic or endothelialization-promoting coating, at least part of which includes fibrin and which completely sheaths all of the filaments of the covering, and wherein at least part of the coating includes heparin.

15. The medical device according to claim 14, wherein one of the covering is cohesively connected to the mesh structure or the coating is cohesively connected to the covering.

16. The medical device according to claim 14, wherein the mesh structure includes mesh elements that are sheathed by a bonding agent which securely connects the covering to the mesh structure.

17. The medical device according to claim 14, wherein the mesh structure includes mesh elements that form webs coupled together into one piece by web connectors.

18. The medical device according to claim 14, wherein the mesh structure includes mesh elements formed by at least one wire.

* * * * *